(12) United States Patent
Baril et al.

(10) Patent No.: US 11,219,463 B2
(45) Date of Patent: Jan. 11, 2022

(54) BILATERAL SPRING FOR SURGICAL INSTRUMENTS AND SURGICAL INSTRUMENTS INCLUDING THE SAME

(71) Applicant: Covidien LP, Mansfield, MA (US)

(72) Inventors: Jacob C. Baril, Norwalk, CT (US); Roy J. Pilletere, North Haven, CT (US); Justin Thomas, New Haven, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 272 days.

(21) Appl. No.: 16/433,049

(22) Filed: Jun. 6, 2019

(65) Prior Publication Data

US 2020/0046362 A1 Feb. 13, 2020

Related U.S. Application Data

(60) Provisional application No. 62/717,988, filed on Aug. 13, 2018.

(51) Int. Cl.
*A61B 17/128* (2006.01)
*A61B 17/00* (2006.01)

(52) U.S. Cl.
CPC .. *A61B 17/128* (2013.01); *A61B 2017/00367* (2013.01); *A61B 2017/00477* (2013.01)

(58) Field of Classification Search
CPC ........ A61B 17/128; A61B 2017/00367; A61B 2017/00477; A61B 2017/2922;
(Continued)

(56) References Cited

U.S. PATENT DOCUMENTS 3,120,230 A 2/1964 Skold
3,363,628 A 1/1968 Wood
(Continued)

FOREIGN PATENT DOCUMENTS

AU 2013254887 A1 11/2013
CA 1163889 A 3/1984
(Continued)

OTHER PUBLICATIONS

Extended European Search Report issued in corresponding Appl. No. EP 19191224.5 dated Dec. 13, 2019 (8 pages).

*Primary Examiner* — Shaun L David
*Assistant Examiner* — Joshua T. Hicks

(57) ABSTRACT

A handle assembly of a surgical instrument includes a housing, a trigger pivotably coupled to the housing, a drive bar disposed within the housing and operably coupled to the trigger such that pivoting of the trigger translates the drive bar, and a bilateral spring disposed within the housing and operably coupled to at least one of the trigger or the drive bar. The trigger is movable relative to the housing between first, second, and third positions wherein the first position is disposed between the second and third positions. The bilateral spring includes a compression spring configured to compress upon movement of the trigger in a first direction from the first position towards the second position to establish a first bias, and to compress upon movement of the trigger in a second, opposite direction from the first position towards the third position to establish a second bias.

18 Claims, 7 Drawing Sheets

(58) Field of Classification Search
CPC ........ A61B 17/2909; A61B 2017/2929; A61B 2017/0046; A61B 17/1285
See application file for complete search history.

(56) References Cited

U.S. PATENT DOCUMENTS

| | | | |
|---|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A * | 9/1991 | Simon ................ A61B 17/1285 606/143 |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |

(56) References Cited

U.S. PATENT DOCUMENTS

| | | |
|---|---|---|
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |

(56) References Cited

U.S. PATENT DOCUMENTS

| | | |
|---|---|---|
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |

(56) References Cited

U.S. PATENT DOCUMENTS

| | | |
|---|---|---|
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |

(56) References Cited

U.S. PATENT DOCUMENTS

| | | |
|---|---|---|
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Caslo et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0033356 A1 | 2/2005 | Frank et al. |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |

(56) References Cited

U.S. PATENT DOCUMENTS

| | | |
|---|---|---|
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0190138 A1* | 7/2015 | Whitfield ............ A61B 17/1285 606/143 |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1* | 9/2016 | Gokharu ............ A61B 17/105 |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086823 A1* | 3/2017 | Leimbach ............ A61B 17/068 |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 20 2005 001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 3066995 A1 | 9/2016 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017059587 A1 | 4/2017 |
| WO | 2017124217 A1 | 7/2017 |
| WO | 2018035796 A1 | 3/2018 |

* cited by examiner

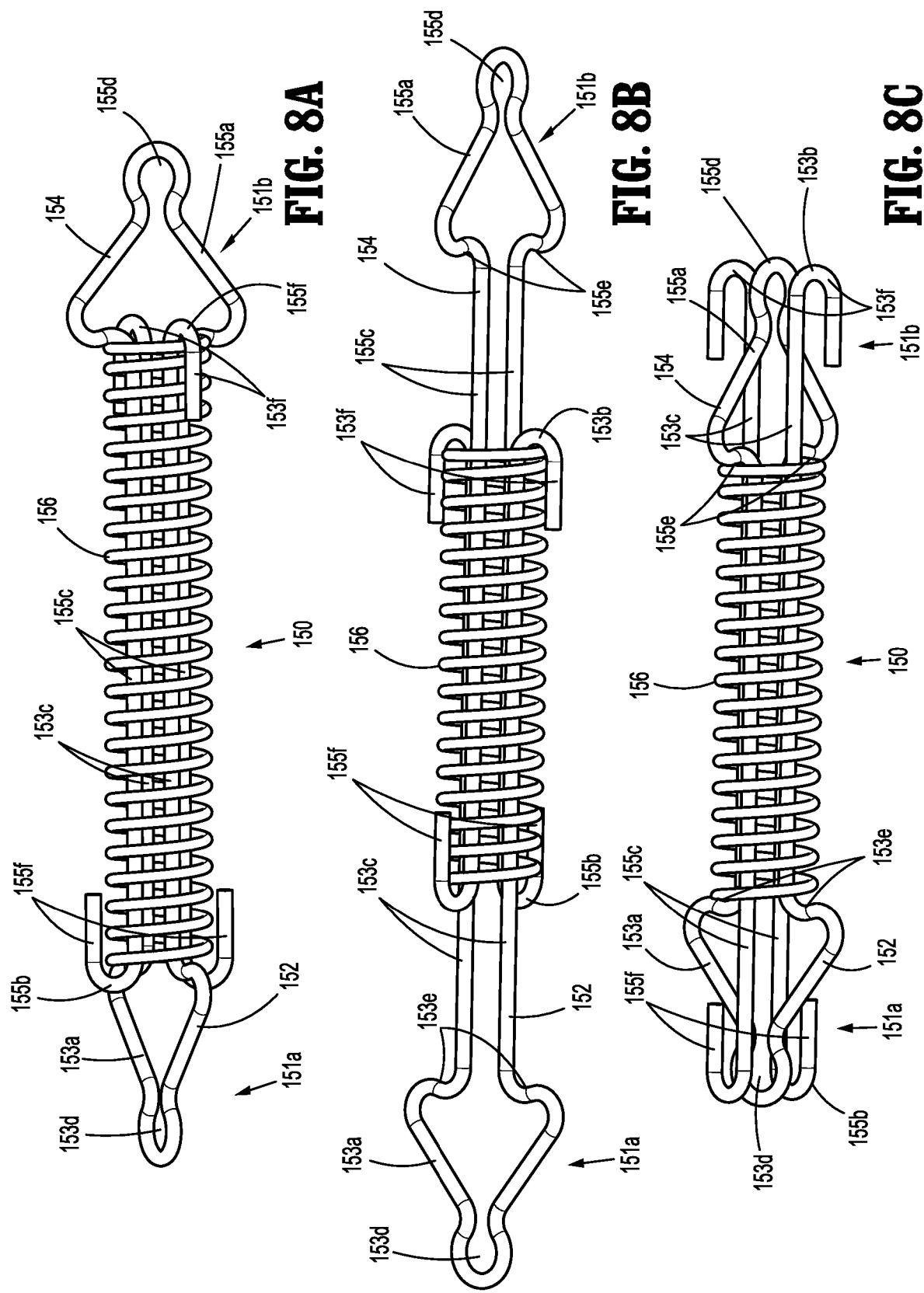

BILATERAL SPRING FOR SURGICAL INSTRUMENTS AND SURGICAL INSTRUMENTS INCLUDING THE SAME

CROSS-REFERENCE TO RELATED APPLICATION

This application claims the benefit of and priority to U.S. Provisional Patent Application No. 62/717,988 filed Aug. 13, 2018, the entire disclosure of which is incorporated by reference herein.

BACKGROUND

Technical Field

The present disclosure relates to surgical instruments such as, for example, surgical clip appliers. More particularly, the present disclosure relates to a bilateral spring for surgical instruments and a surgical instrument including the same.

Description of Related Art

Surgical clip appliers are used for a number of distinct and useful surgical procedures. Surgical clip appliers having various sizes (e.g., diameters), that are configured to apply a variety of diverse surgical clips are capable of applying a single or multiple surgical clips during an entry to the body cavity. Such surgical clips are typically fabricated from a biocompatible material and are usually compressed over tissue. Once applied to tissue, the compressed surgical clip terminates the flow of fluid therethrough.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

A handle assembly of a surgical instrument, in accordance with an aspect of the present disclosure, includes a housing, a trigger, a drive bar, and a bilateral spring. The trigger is pivotably coupled to the housing and movable relative thereto between a first position, a second position, and a third position. The first position is disposed between the second and third positions. The drive bar is disposed within the housing and operably coupled to the trigger such that pivoting of the trigger translates the drive bar.

The bilateral spring is disposed within the housing and operably coupled to at least one of the trigger or the drive bar. The bilateral spring includes a compression spring configured to compress upon movement of the trigger in a first direction from the first position towards the second position to establish a first bias biasing the trigger back towards the first position. The compression spring is also configured to compress upon movement of the trigger in a second, opposite direction from the first position towards the third position to establish a second bias biasing the trigger back towards the first position.

In aspects of the present disclosure, movement of the trigger in the first direction from the first position towards the second position compresses the bilateral spring to thereby compress the compression spring to establish the first bias. Additionally or alternatively, movement of the trigger in the second, opposite direction from the first position towards the third position extends the bilateral spring to compress the compression spring to establish the second bias.

In aspects of the present disclosure, at least one linkage operably couples the trigger and the drive bar such that pivoting of the trigger translates the drive bar. In such aspects, the bilateral spring may be coupled between two or more of the housing, the trigger, the drive bar, or the at least one linkage.

In aspects of the present disclosure, the bilateral spring includes first and second arms each disposed in oppositely-facing directions relative to one another and overlapping one another. In such aspects, the compression spring is disposed about overlapping portions of the first and second arms. Additionally, each of the first and second arms may include an attachment end portion and a retention end portion, wherein the attachment end portions are configured to facilitate operable coupling of the bilateral spring within the housing and wherein the retention end portions are configured to retain the compression spring therebetween.

In aspects of the present disclosure, a latch mechanism is operably coupled to the housing and configured to releasably engage an elongated assembly inserted into the housing. Additionally or alternatively, a rotation knob assembly is rotatably supported at a distal portion of the housing.

In aspects of the present disclosure, the housing includes a body portion and a fixed handle portion. In such aspects, the trigger is pivotable away from the fixed handle portion from the first position to the second position and pivotable towards the fixed handle portion from the first position to the third position.

A surgical instrument, provided in accordance with further aspects of the present disclosure, includes a housing, an elongated assembly extending distally from the housing and supporting an end effector towards a distal end thereof, a trigger pivotably coupled to the housing, a drive bar disposed within the housing and operably coupled to the trigger such that pivoting of the trigger translates the drive bar to actuate the end effector, and a bilateral spring disposed within the housing and operably coupled to at least one of the trigger or the drive bar. The trigger is and movable relative to the housing between a first position, a second position, and a third position wherein the first position is disposed between the second and third positions.

The bilateral spring includes a compression spring configured to compress upon movement of the trigger in a first direction from the first position towards the second position to establish a first bias biasing the trigger back towards the first position, and to compress upon movement of the trigger in a second, opposite direction from the first position towards the third position to establish a second bias biasing the trigger back towards the first position.

In aspects of the present disclosure, movement of the trigger in the first direction from the first position towards the second position compresses the bilateral spring to thereby compress the compression spring to establish the first bias. Additionally or alternatively, movement of the trigger in the second, opposite direction from the first position towards the third position extends the bilateral spring to compress the compression spring to establish the second bias.

In aspects of the present disclosure, at least one linkage operably couples the trigger and the drive bar such that pivoting of the trigger translates the drive bar.

In aspects of the present disclosure, the bilateral spring includes first and second arms each disposed in oppositely-facing directions relative to one another and overlapping one another. In such aspects, the compression spring is disposed about overlapping portions of the first and second arms. Additionally, each of the first and second arms may include an attachment end portion and a retention end portion, wherein the attachment end portions are configured to facilitate operable coupling of the bilateral spring within the housing and wherein the retention end portions are configured to retain the compression spring therebetween.

In aspects of the present disclosure, a latch mechanism is operably coupled to the housing and configured to releasably engage an elongated assembly inserted into the housing. Additionally or alternatively, a rotation knob assembly is rotatably supported at a distal portion of the housing.

In aspects of the present disclosure, the housing includes a body portion and a fixed handle portion. In such aspects, the trigger is pivotable away from the fixed handle portion from the first position to the second position and pivotable towards the fixed handle portion from the first position to the third position.

In aspects of the present disclosure, engagement of the elongated assembly with the housing urges the trigger from the first position to the second position against the first bias of the bilateral spring.

BRIEF DESCRIPTION OF THE DRAWINGS

Aspects and features of the presently-disclosed bilateral spring for surgical clip instruments and surgical instruments including the same are described in detail with reference to the drawing figures wherein like reference numerals identify similar or identical structural elements and:

FIGS. 8A-8C are side views of the bilateral spring of FIG. 6 in a neutral position, an extended position, and a compressed position, respectively.

DETAILED DESCRIPTION

The present disclosure provides a bilateral spring for surgical instruments and surgical instruments including the same. Although detailed herein as incorporated into a surgical clip applier, the bilateral spring of the present disclosure may alternatively be incorporated into any suitable surgical instrument.

Figure 1:
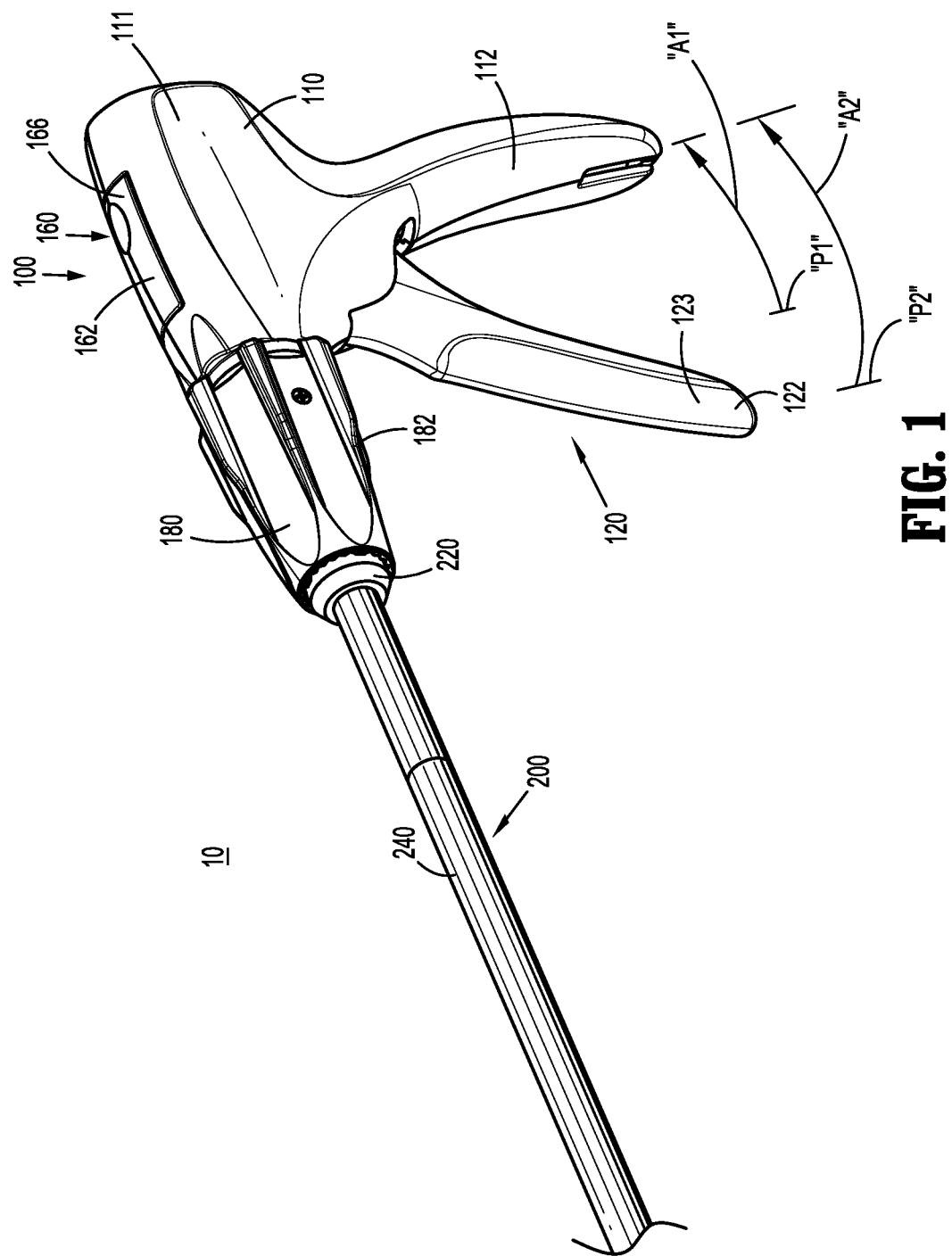
FIG. 1 is a front, perspective view of a surgical clip applier provided in accordance with the present disclosure including a handle assembly having an elongated assembly engaged therewith.
Figure 2:
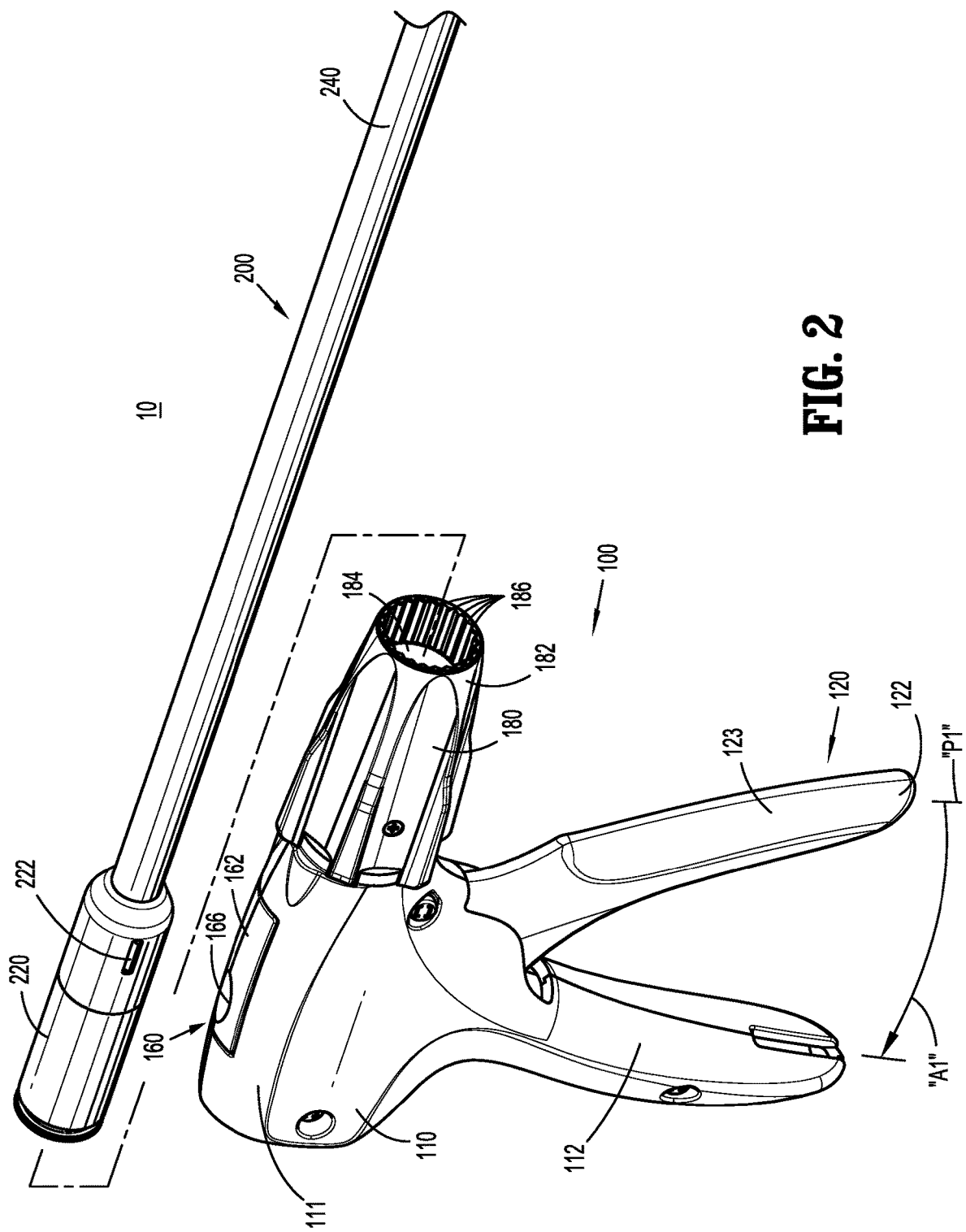
FIG. 2 is front, perspective view of the surgical clip applier of FIG. 1 with the elongated assembly removed from the handle assembly.

Turning to FIGS. 1-2, a surgical clip applier embodying the aspects and features of the present disclosure is shown generally identified by reference numeral 10. Surgical clip applier 10 generally includes a handle assembly 100 and a plurality of elongated assemblies 200, 300 (FIG. 3B) selectively connectable to handle assembly 100. Handle assembly 100 is configured to operate each of the plurality of elongated assemblies 200, 300 (FIG. 3B) upon connection thereto, and may be configured as a sterilizable, reusable component such that handle assembly 100 may be repeatedly used with different and/or additional elongated assemblies 200, 300 (FIG. 3B) during the course of one or more surgical procedures. The elongated assemblies 200, 300 (FIG. 3B) may be configured as single-use disposable components, limited-use disposable components, or reusable components, depending upon a particular purpose and/or the configuration of the particular elongated assembly. In either configuration, the need for multiple handle assemblies 100 is obviated and, instead, the surgeon need only select an appropriate elongated assembly 200, 300 (FIG. 3B) and connect that elongated assembly to handle assembly 100 in preparation for use.

Figure 3A:
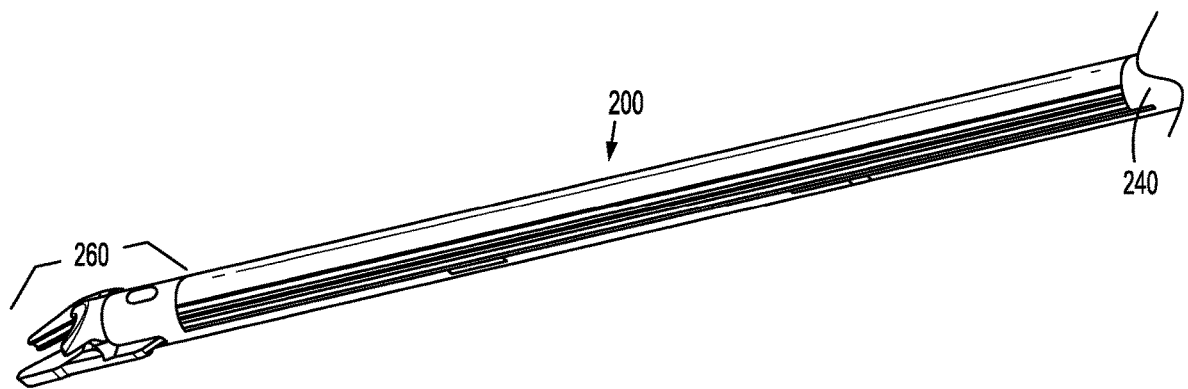
FIG. 3A is a side, perspective view of a distal end portion of the elongated assembly of FIGS. 1 and 2.
Figure 3B:
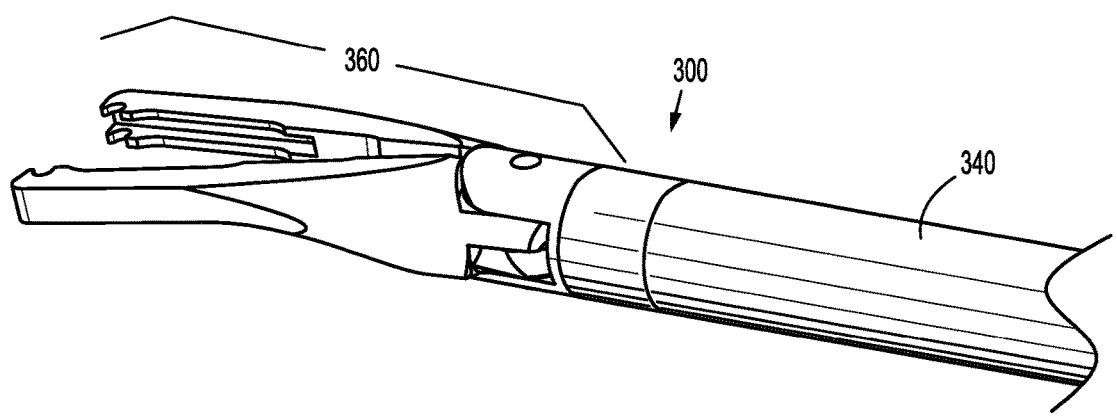
FIG. 3B is a side, perspective view of a distal end portion of another elongated assembly configured for use with the surgical clip applier of FIG. 1.

With additional reference to FIGS. 3A and 3B, as noted above, handle assembly 100 is configured for use with different elongated assemblies such as, for example, elongated assembly 200 (FIGS. 1-3A) and elongated assembly 300 (FIG. 3B). Elongated assemblies 200, 300 are described briefly below. A more detailed discussion of elongated assemblies, e.g., elongated assemblies 200, 300, configured for use with handle assembly 100 can be found in International Appln. Pub. Nos. WO2018/035796, WO2017/124217, and/or WO2017/059587, the entire content of each of which is hereby incorporated herein by reference.

Referring to FIGS. 1-3A, elongated assembly 200 generally includes a proximal hub 220, an elongated shaft 240 extending distally from proximal hub 220, an end effector 260 disposed towards a distal end portion of elongated shaft 240, and an inner drive assembly 280 (FIG. 4) operably coupled between handle assembly 100 and end effector 260 when elongated assembly 200 is engaged with handle assembly 100 to enable the sequential firing of at least one surgical clip (not shown) about tissue. End effector 260 of elongated assembly 200 may be configured to fire surgical clips similar to those shown and described in U.S. Pat. No. 7,819,886 or 7,905,890, the entire content of each of which is hereby incorporated herein by reference.

Proximal hub 220 of elongated assembly 200 defines a plurality of indexing protrusions 222 annularly disposed thereabout towards a distal end portion thereof. Indexing protrusions 222, as detailed below, are configured for slidable receipt within longitudinally-extending grooves 186 defined within outer knob 182 of rotation knob assembly 180 to rotationally fix proximal hub 220 of elongated assembly 200 relative to rotation knob assembly 180 upon insertion of proximal hub 220 therethrough. As such, in use, rotation of outer knob 182 of rotation knob assembly 180 relative to housing 110 of handle assembly 100 effects corresponding rotation of elongated assembly 200 relative to housing 110.

Referring to FIG. 3B, in conjunction with FIGS. 1 and 2, elongated assembly 300 generally includes a proximal hub (not shown), an elongated shaft 340 extending distally from the proximal hub, an end effector 360 disposed towards a distal end portion of elongated shaft 340, and an inner drive assembly (not shown) operably coupled between handle assembly 100 and end effector 360 when elongated assembly 300 is engaged with handle assembly 100 to enable grasping and/or manipulation of tissue, retrieval of a surgical clip, and firing of the surgical clip about tissue. It is contemplated that end effector 360 of elongated assembly 300 may be configured to fire surgical clips similar to those shown and described in U.S. Pat. No. 4,834,096, the entire content of which is hereby incorporated herein by reference.

The proximal hub (not shown) of elongated assembly 300 includes indexing protrusions similarly as detailed above with respect to proximal hub 220 of elongated assembly 200 (see FIG. 2) such that elongated assembly 300 is rotationally fix relative to rotation knob assembly 180 upon insertion of proximal hub 220 therethrough to enable rotation of elongated assembly 300 relative to housing 110 of handle assembly 100 in response to rotation of outer knob 182 of rotation knob assembly 180 relative to housing 110.

Referring to FIGS. 1-5, although exemplary elongated assemblies 200, 300 are detailed above, it is contemplated that various other elongated assemblies for performing various different surgical tasks and/or having various different configurations may likewise be utilized with handle assembly 100. As can be appreciated, the actuation length required to actuate an elongated assembly may vary between different elongated assemblies such as, for example, depending upon the particular configuration of the elongated assembly. Handle assembly 100, as detailed below, is configured for use with various different elongated assemblies having various different actuation lengths without providing any dead space at the beginning or end of the actuation stroke of trigger 122 of actuation mechanism 120 of handle assembly 100.

Handle assembly 100 of surgical clip applier 10 generally includes a housing 110, an actuation mechanism 120 operably associated with housing 110, a latch assembly 160 operably associated with housing 110, and a rotation knob assembly 180 operably coupled to a distal portion of housing 110. Housing 110 of handle assembly 100 supports and/or encloses the operating components of handle assembly 100 and defines a body portion 111 and a fixed handle portion 112 depending from body portion 111. Body portion 111 of housing 110 includes an internal pivot post 114 extending transversely within body portion 111 and a distal opening 118 through which a proximal end portion of elongated assembly 200 extends when elongated assembly 200 is engaged with handle assembly 100.

Figure 4:
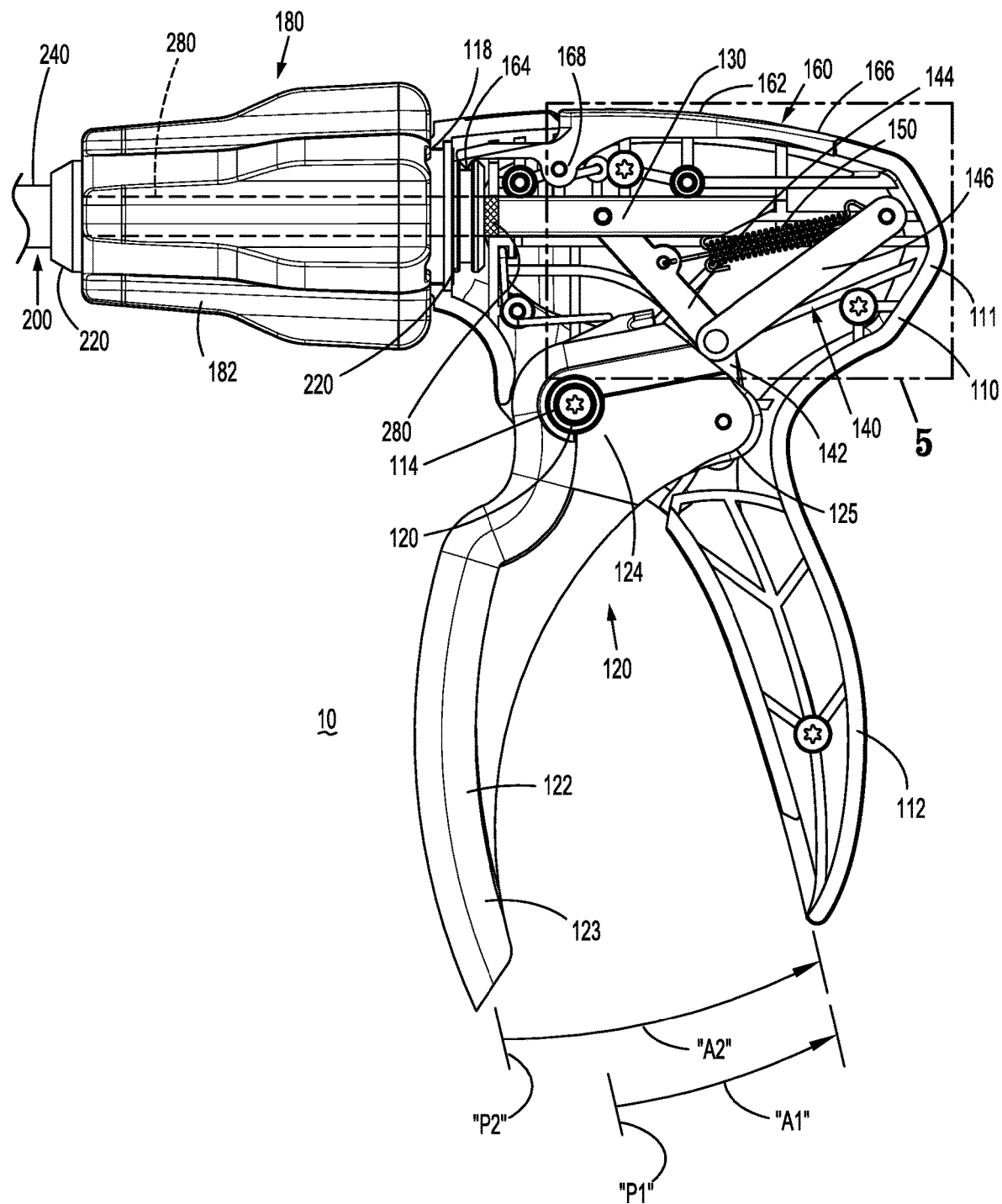
FIG. 4 is a side view of a proximal portion of the surgical clip applier of FIG. 1 with a portion of the housing of the handle assembly removed to illustrate the internal components therein.
Figure 5:
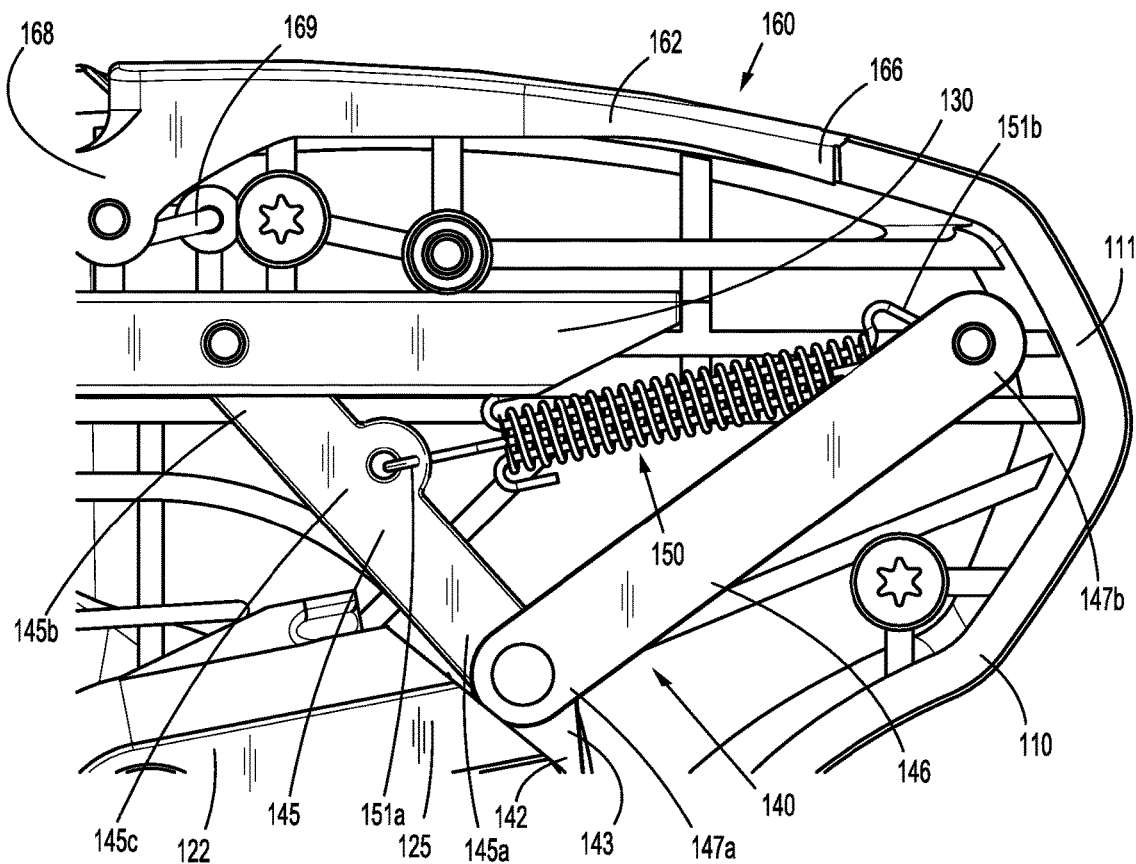
FIG. 5 is an enlarged, side view of the area of detail indicated as "5" in FIG. 4.
Figure 6:
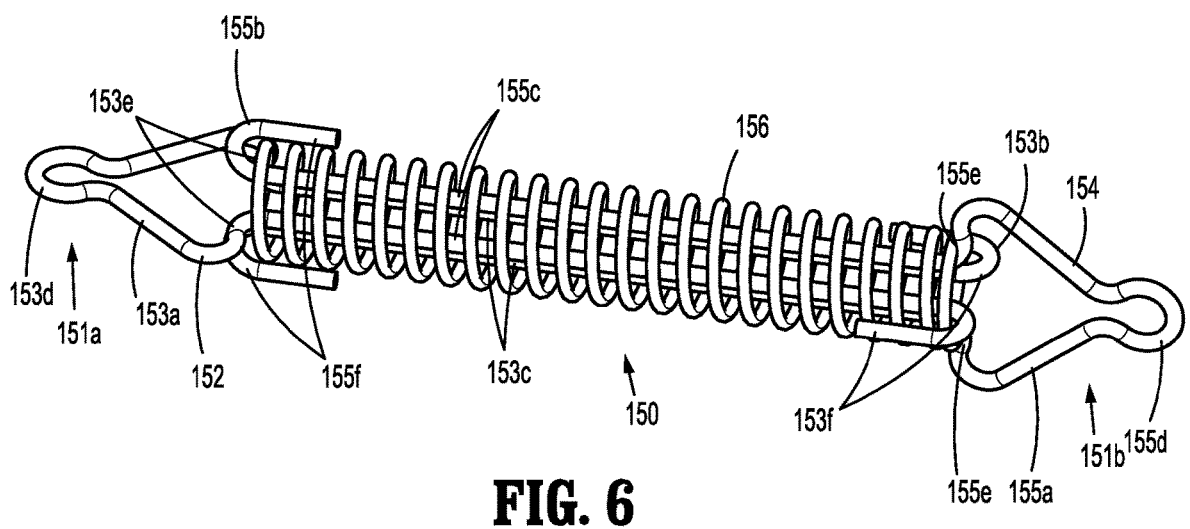
FIG. 6 is a perspective view of a bilateral spring provided in accordance with the present disclosure and configured for use with the surgical clip applier of FIG. 1.
Figure 7:
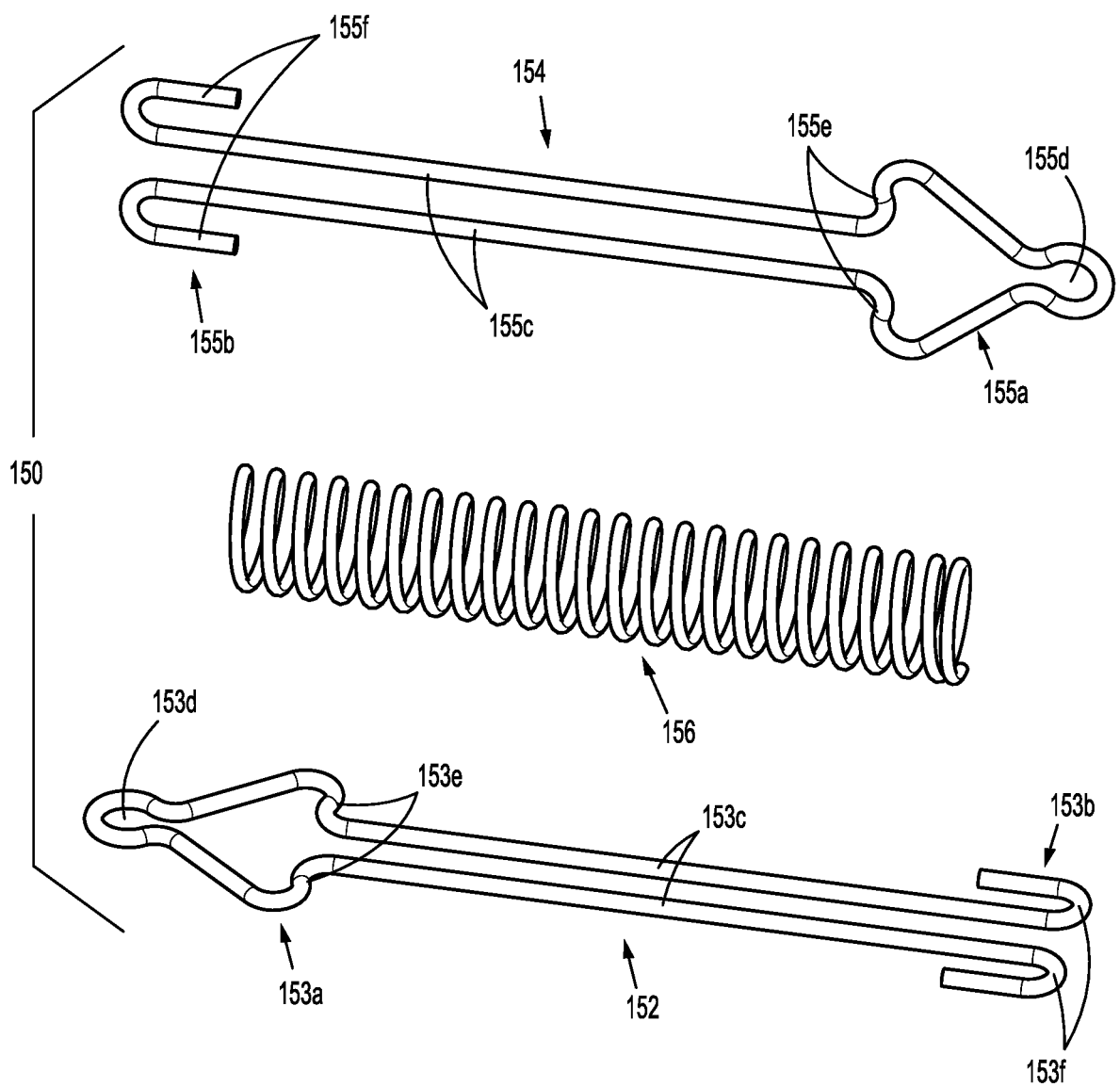
FIG. 7 is an exploded, perspective view of the bilateral spring of FIG. 6.

With particular reference to FIGS. 4-5, actuation mechanism 120 is operably supported by housing 110 and includes a trigger 122, a drive bar 130, a linkage assembly 140, and a bilateral spring 150. Trigger 122 includes a grasping portion 123, an intermediate pivot portion 124, and a proximal extension 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126 that is configured to receive pivot post 114 of housing 110 so as to enable pivoting of trigger 122 about pivot post 114 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension 125 of trigger 122 is disposed on an opposite side of intermediate pivot portion 124 and, thus, pivot post 114, as compared to grasping portion 123 of trigger 122. As such, pivoting of grasping portion 123 to rotate in one direction, e.g., proximally towards fixed handle portion 112, pivots proximal extension 125 to rotate in the opposite direction, e.g., distally.

Drive bar 130 is slidably disposed within body portion 111 of housing 110 in longitudinal alignment with an inner drive assembly of an elongated assembly engaged with handle assembly 100, e.g., inner drive assembly 280 of elongated assembly 200 (see FIG. 4). In this manner, when elongated assembly 200 is engaged with handle assembly 100, distal sliding of drive bar 130 through body portion 111 of housing 110 urges drive bar 130 distally to, in turn, urge the inner drive assembly 280 (or portion(s) thereof) distally to actuate end effector 260 of elongated assembly 200, e.g., to apply, form, or close a surgical clip supported at end effector 260.

Continuing with reference to FIGS. 4-5, linkage assembly 140 operably couples trigger 122 with drive bar 130 and includes a first linkage 142, a second linkage 144, and a third linkage 146. First linkage 142 is pivotably coupled to proximal extension 125 of trigger 122 towards a first end (not shown) of first linkage 142. Second and third linkages 144, 146, respectively, are each pivotably coupled to a second end 143 of first linkage 142 at respective first ends 145a, 147a of second and third linkages 144, 146. A second end 145b of second linkage 144 is pivotably coupled to drive bar 130, while a second end 147b of third linkage 146 is pivotably coupled to body portion 111 of housing 110. Thus, the pivot point between first linkage 142 and proximal extension 125 of trigger 122, the pivot point between first linkage 142 and second and third linkages 144, 146, respectively, and the pivot point between second linkage 144 and drive bar 130 are movable pivot points (e.g., movable relative to housing 110), while the pivot point between third linkage 146 and housing 110 is a fixed pivot point (e.g., fixed relative to housing 110).

Upon actuation of trigger 122, e.g., proximal pivoting of grasping portion 123 of trigger 122, proximal extension 125 is moved in a counter-clockwise direction (from the orientation illustrated in FIG. 4), thereby urging first linkage 142 towards drive bar 130. This movement of first linkage 142 towards drive bar 130, in turn, urges first ends 145a, 147a of second and third linkages 144, 146, respectively, towards drive bar 130 to, in turn, urge second end 145b of second linkage 144 distally such that drive bar 130 is translated distally through body portion 111 of housing 110. Return of trigger 122 distally, e.g., clockwise from the orientation illustrated in FIG. 4, effects opposite movement of linkages 142, 144, 146 to thereby return drive bar 130 proximally.

Bilateral spring 150 is coupled at a first end 151a thereof to an intermediate portion 145c of second linkage 144, e.g., between first and second ends 145a, 145b, respectively, thereof, and at a second end 151b thereof to second end 147b of third linkage 146 and/or to body portion 111 of housing 110 at the pivot point where second end 147b of third linkage 146 is pivotably coupled to body portion 111 of housing 110. In this manner, bilateral spring 150 is extended from its neutral position, corresponding to a position "P1" of trigger 122, in response to actuation of trigger 122 proximally from position "P1" towards fixed handle portion 112 of housing 110, and is compressed from its neutral position in response to movement of trigger 122 distally from position "P1," e.g., away from fixed handle portion 112 of housing 110. Other suitable positionings wherein bilateral spring 150 is compressed upon movement of trigger 122 from position "P1" in one direction and extended upon movement of trigger 122 from position "P1" in a second, opposite direction are also contemplated. In particular, bilateral spring 150 may be coupled between any two or more of housing 110, trigger 122, drive bar 130, or linkages 142, 144, 146 whereby bilateral spring 150 achieves the above-detailed compression and extension.

Bilateral spring 150 provides a biasing force in response to both the compression of bilateral spring 150 and the extension of bilateral spring 150. More specifically, when bilateral spring 150 is extended, e.g., after trigger 122 is actuated proximally to move drive bar 130 distally, bilateral spring 150 provides a biasing force urging bilateral spring 150 to return towards its neutral position, e.g., thereby biasing trigger 122 distally and drive bar 130 proximally. Similarly, when bilateral spring 150 is compressed, e.g., when an elongated assembly is engaged with handle assembly 100 to move drive bar 130 proximally and trigger 122 distally, bilateral spring 150 provides a biasing force urging bilateral spring 150 to return towards its neutral position, e.g., thereby biasing trigger 122 proximally and returning drive bar 130 distally (when allowed, such as when the elongated assembly is removed from handle assembly 100). The configuration of bilateral spring 150 and features thereof are described in detail below with respect to FIGS. 6-8C.

Referring again to FIGS. 1-5, latch assembly 160 is configured to facilitate releasable locking engagement of an elongated assembly, e.g., elongated assembly 200, with handle assembly 100. Latch assembly 160, more specifically, includes a pivoting lever arm 162 operably disposed on and extending into body portion 111 of housing 110. Lever arm 162 includes an engagement finger 164 (FIG. 4) disposed towards one end thereof and a manipulatable portion 166 disposed towards the other end thereof with a pivot portion 168 disposed therebetween. Thus, upon depression of manipulatable portion 166 into housing 110 from a locked position to an unlocked position, engagement finger 164 is withdrawn upwardly and, upon release of manipulatable portion 166 and return thereof to the locked position, engagement finger 164 is returned downwardly. A torsion spring 169 (FIG. 5) disposed about pivot portion 168, or other suitable biasing spring in any suitable position, may be provided to bias lever arm 162 towards the locked position, although other configurations are also contemplated.

Rotation knob assembly 180 is configured to receive a proximal end portion of an elongated assembly, e.g., elongated assembly 200, and to enable selective rotation thereof relative to housing 110. Rotation knob assembly 180 includes an outer knob 182 rotatably coupled to body portion 111 of housing 110 and extending distally therefrom. Outer knob 182 defines a lumen 184 extending therethrough in communication with distal opening 118 of body portion 111 of housing 110 to enable insertion of a proximal portion of elongated assembly 200 therethrough and into operable engagement within housing 110. Rotation knob 182 defines grooves 186 on an interior surface thereof and arranged annularly about lumen 184 to enable rotatable coupling of elongated assembly 200 therewith, as noted above.

Referring generally to FIGS. 1-5, insertion and engagement of an elongated assembly, e.g., elongated assembly 200, with handle assembly 100 and use of the same are described. It is appreciated that insertion and engagement of other elongated assemblies, e.g., elongated assembly 300, is effected in a similar manner. Initially, prior to engagement of elongated assembly 200 with handle assembly 100, trigger 122 is maintained in first position "P1" under the bias of bilateral spring 150 with bilateral spring 150 disposed in its neural position.

In order to engage elongated assembly 200 with handle assembly 100, proximal hub 220 of elongated assembly 200 is inserted through into outer knob 182 of rotation knob assembly 180 and through lumen 184 thereof. Proximal hub 220 is advanced further proximally through distal opening 118 of housing 110 and, eventually, engagement finger 164 of latch assembly 160 cams over the proximal end of proximal hub 220 and into engagement therewith to rotatably engage proximal hub 220 relative to housing 110. Upon insertion of proximal hub 220 through rotation knob assembly 180, as noted above, indexing protrusions 222 of proximal hub 220 are received within longitudinally-extending grooves 186 of outer knob 182 to rotationally fix proximal hub 220 relative to outer knob 182 (see FIG. 2).

Upon insertion and engagement of elongated assembly 200 within handle assembly 100, the proximal portion of inner drive assembly 280 of elongated assembly 200 is urged into contact with the distal portion of drive bar 130 and urges drive bar 130 proximally, against the bias of bilateral spring 150, thereby urging trigger 122 distally to a second position "P2" wherein trigger 122 defines a second actuation stroke length "A2" longer than first actuation stroke length "A1" of trigger 122 when trigger 122 is disposed in position "P1." Drive bar 130 is urged proximally against the bias of bilateral spring 150 to thereby compress bilateral spring; that is, ends 151a, 151b of bilateral spring 150 are urged inwardly towards one another.

Depending upon the particular configuration of the elongated assembly engaged with handle assembly 100, the inner drive assembly thereof may urge drive bar 130 further proximally, not as far proximally, or may simply be moved into abutment with drive bar 130 without significantly moving drive bar 130 proximally. As such, depending upon the elongated assembly engaged, the starting positions of trigger 122 and drive bar 130 may be shifted (while the fully actuated positions thereof remain the same) such that, in use, the actuation stroke of trigger 122 and the drive distance of drive bar 130 are reduced according to the actuation length of the inner drive assembly of the elongated assembly engaged with handle assembly 100, thereby eliminating dead space during actuation of trigger 122. More specifically, drive bar 130 is biased by bilateral spring 150 such that trigger 122 is biased towards first position "P1," corresponding to a minimum stroke length of trigger 122 and, upon engagement of an elongated assembly therewith, drive bar 130 is moved proximally against the bias of bilateral spring 150 via the inner drive assembly of the elongated assembly, thereby moving trigger 122 distally (increasing the stroke length thereof) from first position "P1" to a position corresponding to the appropriate stroke length for that elongated assembly, e.g., position "P2." As noted above, movement of trigger 122 from position "P1" to position "P2" compresses bilateral spring 150.

With elongated assembly 200 engaged with handle assembly 100, as detailed above, handle assembly 100 may be manipulated and/or outer knob 182 rotated to position end effector 260 (FIG. 3A) of elongated assembly 200 about tissue to be treated. Once end effector 260 is positioned as desired, trigger 122 is pivoted towards fixed handle portion 112 of housing 110, e.g., from position "P2" beyond position "P1" to a fully-actuated position. This pivoting of trigger 122 moves linkages 142, 144, 146 of linkage assembly 140 to thereby urge drive bar 130 distally through housing 110 to drive inner drive assembly 280 (or portion(s) thereof) of elongated assembly 200 distally to fire and form a surgical clip from end effector 260 (FIG. 3A) about tissue. Movement of trigger 122 from position "P2" to the fully-actuated position thereof extends bilateral spring 150.

When firing is complete, trigger 122 may be released such that trigger 122 is returned distally, e.g., from the fully-actuated position, through position "P1," to position "P2," and, thus, drive bar 130 is returned proximally, both under the bias of bilateral spring 150. Thus, inner drive assembly 280 and end effector 260 (FIG. 3A) of elongated assembly 200 are returned to their initial, un-actuated positions. The returns of trigger 122 and drive bar 130 are provided by bilateral spring 150. The above may then be repeated to fire and form several surgical clips about tissue, as necessary.

In order to disengage elongated assembly 200 from handle assembly 100, e.g., for cleaning and/or sterilization, or to replace elongated assembly 200 with another elongated assembly, manipulatable portion 166 of latch assembly 160 is depressed inwardly into housing 110 to disengage proximal hub 220 of elongated assembly 200 therefrom, thus enabling elongated assembly 200 to be withdrawn distally from housing 110 and rotation knob assembly 180. Upon withdrawal of elongated assembly 200 from housing 110, bilateral spring 150 urges drive bar 130 distally and trigger 122 proximally from position "P2" back to position "P1."

Turning to FIGS. 6-8C, in conjunction with FIGS. 1 and 4, as demonstrated above, bilateral spring 150 provides a biasing force back towards its neutral position in response to both extension of bilateral spring 150, e.g., when trigger 122 is actuated proximally from position "P2," and compression of bilateral spring 150, e.g., upon insertion of elongated assembly 200 into handle assembly 200 to urge trigger 122 distally from position "P1" to position "P2." The configuration and features of bilateral spring 150 enabling this functionality are detailed below, keeping in mind that bilateral spring 150 may be utilized with different surgical instruments and/or for different multi-direction biasing purposes. Likewise, different configurations of bilateral spring 150 for use with surgical clip applier 10 to achieve the above are also contemplated.

Bilateral spring 150 includes a first arm 152, a second arm 154, and a compression spring 156. First and second arms 152, 154 are identical in configuration and are assembled in opposite-facing directions at orientations 90 degrees offset from one another (although other orientations may also be achieved as a result of relative rotation between arms 152, 154). First and second arms 152, 154 are each formed from a single piece of wire bent to define the features thereof (although other configurations are also contemplated); more specifically, each arm 152, 154 includes an attachment end portion 153a, 155a, a retention end portion 153b, 155b, and a pair of spaced-apart rails 153c, 155c extending between the respective attachment end portions 153a, 155a thereof and the respective retention end portions 153b, 155b thereof. Attachment end portions 153a, 155a correspond to the respective first and second ends 151a, 151b of bilateral spring 150 and include attachment features, e.g., loops 153d, 155d, to enable attachment of first end 151a to intermediate portion 145c of second linkage 144 (see FIG. 5) and second end 151b to second end 147b of third linkage 146 (see FIG. 5). Each attachment end portions 153a, 155a also includes a pair of shoulders 153e, 155e formed between the respective loop 153d, 155d thereof and the respective spaced-apart rails 153c, 155c thereof. Retention end portions 153b, 155b of arms 152, 154 include retention features, e.g., hooks 153f, 155f, extending from the ends of the respective spaced-apart rails 153c, 155c adjacent retention end portions 153b, 155b thereof.

Compression spring 156 is disposed about the spaced-apart rails 153c, 155c of each of first and second arms 152, 154 and is captured, towards first end 151a thereof, via shoulders 153e of first arm 152 and hooks 155f of second arm 154, and towards second end 151b thereof via hooks 153f of first arm 152 and shoulders 155e of second arm 154.

Referring now to FIGS. 8A-8C, in conjunction with FIG. 4, as a result of the above-detailed configuration of bilateral spring 150, bilateral spring 150 provides, as also detailed above, a biasing force back towards its neutral position in response to both extension of bilateral spring 150 and compression of bilateral spring 150. The neutral position of bilateral spring 150 is illustrated in FIG. 8A. Extension of bilateral spring 150 from this neutral position to the extended position, illustrated in FIG. 8B, occurs when (one or both of) attachment end portions 153a, 155a are pulled apart from one another to expand bilateral spring 150. As bilateral spring 150 is expanded, shoulders 153e, 155e are moved apart from one another, away from compression spring 156, and hooks are 153f, 155f are moved towards one another, compressing compression spring 156 therebetween. This compression of compression spring 156 builds up potential energy that provides the bias of bilateral spring 150 from the extended position (FIG. 8B) towards the neutral position (FIG. 8A).

Compression of bilateral spring 150 from the neutral position to the compressed position, illustrated in FIG. 8C, occurs when (one or both of) attachment end portions 153a, 155a are urged towards one another to compress bilateral spring 150. As bilateral spring 150 is compressed, hooks 153f, 155f are moved apart from one another, away from compression spring 156, and shoulders 153e, 155e are moved towards one another, compressing compression spring 156 therebetween. This compression of compression spring 156 builds up potential energy that provides the bias of bilateral spring 150 from the compressed position (FIG. 8C) towards the neutral position (FIG. 8A).

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A handle assembly of a surgical instrument, comprising:
　a housing;
　a trigger pivotably coupled to the housing and movable relative thereto between a first position, a second position, and a third position, wherein the first position is disposed between the second and third positions;
　a drive bar disposed within the housing and operably coupled to the trigger such that pivoting of the trigger translates the drive bar; and
　a bilateral spring disposed within the housing and operably coupled to at least one of the trigger or the drive bar, the bilateral spring including a compression spring, wherein the compression spring is configured to compress upon movement of the trigger in a first direction from the first position towards the second position to establish a first bias biasing the trigger back towards the first position, and to compress upon movement of the trigger in a second, opposite direction from the first position towards the third position to establish a second bias biasing the trigger back towards the first position, wherein movement of the trigger in the second, opposite direction from the first position towards the third position extends the bilateral spring to compress the compression spring to establish the second bias.

2. The handle assembly according to claim 1, wherein movement of the trigger in the first direction from the first position towards the second position compresses the bilateral spring to thereby compress the compression spring to establish the first bias.

3. The handle assembly according to claim 1, further comprising at least one linkage operably coupling the trigger and the drive bar such that pivoting of the trigger translates the drive bar.

4. The handle assembly according to claim 3, wherein the bilateral spring is coupled between at least two of the housing, the trigger, the drive bar, or the at least one linkage.

5. The handle assembly according to claim 1, further including a latch mechanism operably coupled to the housing and configured to releasably engage an elongated assembly inserted into the housing.

6. The handle assembly according to claim 1, further comprising a rotation knob assembly rotatably supported at a distal portion of the housing.

7. The handle assembly according to claim 1, wherein the housing includes a body portion and a fixed handle portion, the trigger pivotable away from the fixed handle portion from the first position to the second position and pivotable towards the fixed handle portion from the first position to the third position.

8. A handle assembly of a surgical instrument, comprising:
 a housing;
 a trigger pivotably coupled to the housing and movable relative thereto between a first position, a second position, and a third position, wherein the first position is disposed between the second and third positions;
 a drive bar disposed within the housing and operably coupled to the trigger such that pivoting of the trigger translates the drive bar; and
 a bilateral spring disposed within the housing and operably coupled to at least one of the trigger or the drive bar, the bilateral spring including a compression spring, wherein the compression spring is configured to compress upon movement of the trigger in a first direction from the first position towards the second position to establish a first bias biasing the trigger back towards the first position, and to compress upon movement of the trigger in a second, opposite direction from the first position towards the third position to establish a second bias biasing the trigger back towards the first position, wherein the bilateral spring includes first and second arms each disposed in oppositely-facing directions relative to one another and overlapping one another, wherein the compression spring is disposed about overlapping portions of the first and second arms.

9. The handle assembly according to claim 8, wherein each of the first and second arms includes an attachment end portion and a retention end portion, the attachment end portions configured to facilitate operable coupling of the bilateral spring within the housing and the retention end portions configured to retain the compression spring therebetween.

10. A surgical instrument, comprising:
 a housing;
 an elongated assembly extending distally from the housing and supporting an end effector towards a distal end thereof;
 a trigger pivotably coupled to the housing and movable relative thereto between a first position, a second position, and a third position, wherein the first position is disposed between the second and third positions;
 a drive bar disposed within the housing and operably coupled to the trigger such that pivoting of the trigger translates the drive bar to actuate the end effector; and
 a bilateral spring disposed within the housing and operably coupled to at least one of the trigger or the drive bar, the bilateral spring including a compression spring, wherein the compression spring is configured to compress upon movement of the trigger in a first direction from the first position towards the second position to establish a first bias biasing the trigger back towards the first position, and to compress upon movement of the trigger in a second, opposite direction from the first position towards the third position to establish a second bias biasing the trigger back towards the first position, wherein movement of the trigger in the second, opposite direction from the first position towards the third position extends the bilateral spring to compress the compression spring to establish the second bias.

11. The surgical instrument according to claim 10, wherein movement of the trigger in the first direction from the first position towards the second position compresses the bilateral spring to thereby compress the compression spring to establish the first bias.

12. The surgical instrument according to claim 10, further comprising at least one linkage operably coupling the trigger and the drive bar such that pivoting of the trigger translates the drive bar.

13. The surgical instrument according to claim 10, further including a latch mechanism operably coupled to the housing and configured to releasably engage the elongated assembly therein.

14. The surgical instrument according to claim 10, further comprising a rotation knob assembly rotatably supported at a distal portion of the housing.

15. The surgical instrument according to claim 10, wherein the housing includes a body portion and a fixed handle portion, the trigger pivotable away from the fixed handle portion from the first position to the second position and pivotable towards the fixed handle portion from the first position to the third position.

16. The surgical instrument according to claim 10, wherein engagement of the elongated assembly with the housing urges the trigger from the first position to the second position against the first bias of the bilateral spring.

17. A surgical instrument, comprising:
 a housing;
 an elongated assembly extending distally from the housing and supporting an end effector towards a distal end thereof;
 a trigger pivotably coupled to the housing and movable relative thereto between a first position, a second position, and a third position, wherein the first position is disposed between the second and third positions;

a drive bar disposed within the housing and operably coupled to the trigger such that pivoting of the trigger translates the drive bar to actuate the end effector; and a bilateral spring disposed within the housing and operably coupled to at least one of the trigger or the drive bar, the bilateral spring including a compression spring, wherein the compression spring is configured to compress upon movement of the trigger in a first direction from the first position towards the second position to establish a first bias biasing the trigger back towards the first position, and to compress upon movement of the trigger in a second, opposite direction from the first position towards the third position to establish a second bias biasing the trigger back towards the first position, wherein the bilateral spring includes first and second arms each disposed in oppositely-facing directions relative to one another and overlapping one another, wherein the compression spring is disposed about overlapping portions of the first and second arms.

18. The surgical instrument according to claim 17, wherein each of the first and second arms includes an attachment end portion and a retention end portion, the attachment end portions configured to facilitate operable coupling of the bilateral spring within the housing and the retention end portions configured to retain the compression spring therebetween.

* * * * *